(12) United States Patent
Tsien et al.

(10) Patent No.: US 7,041,821 B2
(45) Date of Patent: *May 9, 2006

(54) SYNTHETIC MOLECULES FOR LABELING HISTIDINE-RICH PROTEINS

(75) Inventors: Roger Y. Tsien, La Jolla, CA (US); Christina Hauser, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/759,762

(22) Filed: Jan. 16, 2004

(65) Prior Publication Data

US 2004/0241749 A1    Dec. 2, 2004

Related U.S. Application Data

(63) Continuation-in-part of application No. 10/346,658, filed on Jan. 16, 2003.

(51) Int. Cl.
*C07D 265/38* (2006.01)
*C07D 311/80* (2006.01)

(52) U.S. Cl. ...................... 544/104; 549/391
(58) Field of Classification Search ............ 544/104; 549/391
See application file for complete search history.

(56) References Cited

U.S. PATENT DOCUMENTS 5,262,333 A    11/1993    Heiman et al.

*Primary Examiner*—Taofiq Solola
(74) *Attorney, Agent, or Firm*—Townsend and Townsend and Crew LLP

(57) ABSTRACT

The invention provides Zn-chelating compounds that are molecularly engineered to bind to a specific target sequence in a protein of interest. The $Zn^{2+}$ ion is far less toxic and promiscuous than nickel and therefore provides an attractive alternative to Ni-based labeling systems. Invention Zn-chelating compounds also do not require oxidizable thiols and therefore can be used in non-reducing environments such as the surface of living cells. In addition, the target sequence is genetically encodable and requires incorporation of only a few amino acids, unlike fusions to fluorescent proteins such as GFP.

19 Claims, 7 Drawing Sheets

Staining Experiments

Transient Transfection of
HEK cells with his$_6$- pdisplay DNA

Ex 540 / Em595  DIC 560

Staining Protocol
Addition of dye in 1μM Zn-buffer
for 10 s, 1X wash with HBSS

Quick wash (1X) with 1mM EDTA

Before After

SEQUENCE LISTING

<160> NUMBER OF SEQ ID NOS: 4

<210> SEQ ID NO 1
<211> LENGTH: 6
<212> TYPE: PRT
<213> ORGANISM: Artificial sequence
<220> FEATURE:
<223> OTHER INFORMATION: Histidine-rich tag sequence

<400> SEQUENCE: 1

```
His His His His His His
1               5
```

```
<210> SEQ ID NO 2
<211> LENGTH: 33
<212> TYPE: PRT
<213> ORGANISM: Artificial sequence
<220> FEATURE:
<223> OTHER INFORMATION: Histidine-rich target sequence

<400> SEQUENCE: 2

Met Arg Gly Ser His His His His His Gly Met Ala Ser Met Thr
1               5                   10                  15

Gly Gly Gln Gln Met Gly Arg Asp Leu Tyr Asp Asp Asp Lys Asp
            20                  25                  30

Pro
```

```
<210> SEQ ID NO 3
<211> LENGTH: 28
<212> TYPE: DNA
<213> ORGANISM: Artificial sequence
<220> FEATURE:
<223> OTHER INFORMATION: PCR primer

<400> SEQUENCE: 3
ggggagatct atgcggggtt ctcatcat                                    28
```

```
<210> SEQ ID NO 4
<211> LENGTH: 25
<212> TYPE: DNA
<213> ORGANISM: Artificial sequence
<220> FEATURE:
<223> OTHER INFORMATION: PCR primer

<400> SEQUENCE: 4
gaatccgcgg cggatcctta tcgtc                                       25
```

SYNTHETIC MOLECULES FOR LABELING HISTIDINE-RICH PROTEINS

This invention was made in part with government support under Grant No. NS27177 awarded by the National Institutes of Health. The United States government may have certain rights in this invention.

BACKGROUND OF THE INVENTION

1. Field of the Invention

The invention relates generally to compounds and methods for labeling recombinant fusion proteins and in particular to small synthetic molecules that react with target sequences.

2. Background Information

Many techniques in the biological sciences require attachment of labels to macromolecules such as polypeptides. For example, the location of a polypeptide within a cell can be determined by attaching a fluorescent label to the polypeptide.

Traditionally, labeling has been accomplished by chemical modification of purified polypeptides. For example, normal procedures for fluorescent labeling require that the polypeptide be covalently reacted in vitro with a fluorescent dye, then repurified to remove excess dye and/or any damaged polypeptide. Using this approach, problems of labeling stoichiometry and disruption of biological activity are often encountered. Furthermore, to study a chemically modified polypeptide within a cell, microinjection can be required. This can be tedious and cannot be performed on a large population of cells.

A variety of site-specific labeling techniques have been developed and utilized with varying degrees of success, though each technique is not without drawbacks. For example, fusion to Green Fluorescent Protein (GFP) and its different color variants is irreversible and sometimes problematic. Due to the large size of GFP proteins, the fusion can perturb the host protein folding and function. Site-directed mutagenesis incorporating a single cysteine has been used to label proteins, but competing thiols are too ubiquitous in cells to allow labeling in situ. Trivalent arsenic mediated cysteine labeling has been used with some success. However, arsenic only binds reduced thiols and is potentially toxic. Labeling of epitope tags with antibodies has been attempted, but antibodies are large, membrane impermeant, and therefore require microinjection or permeabilization of cells. Single chain antibody-hapten labeling can be utilized, however, antibodies do not fold well in reducing environments. Avidin-biotin labeling suffers from the fact that avidin in the cytosol is either toxic or biotin-saturated. Intein-based labeling systems have not yet been demonstrated in live cells. Finally, the hexahistidine-nickel labeling system is potentially undesirable since nickel is promiscuous, toxic, and quenches fluorescence.

Accordingly, a need exists for improved compositions and methods for labeling polypeptides, especially within or on the surface of living cells.

SUMMARY OF THE INVENTION

The present invention provides Zn-chelating compounds that are molecularly engineered to bind to a specific target sequence in a protein of interest. The $Zn^{2+}$ ion is physiologically abundant, is far less toxic than nickel, and therefore provides an attractive alternative to Ni-based labeling systems. The invention Zn-chelating compounds also do not require oxidizable thiols and therefore can be used in non-reducing environments such as the surface of living cells. In addition, the target sequence is genetically encodable and requires incorporation of only a few amino acids, unlike fusions to fluorescent proteins such as GFP.

In a first embodiment, there are provided compounds having the structure:

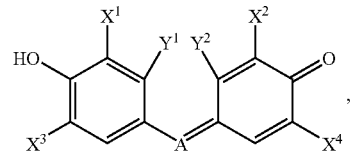

wherein:

$X^1$ and $X^2$ are each independently H, Me, F, Cl, Br, I, $SO_3H$, $CO_2H$, $CONH_2$, $CONMe_2$, CN, or $NO_2$;

$X^3$ is $NHCH_2R$, or $NHSO_2R$, wherein R is $CH_2COOH$, $CH_2CH_2NG^1G^2$, substituted 2-hydroxyphenyl, or a five or six-membered heterocyclic ring, $G^1$ and $G^2$ are H, Me, Et, $CH_2CH_2OH$, or together are $-(CH_2)_4-$, $-(CH_2)_5-$, $-CH_2CH_2OCH_2CH_2-$, or $-CH_2CH_2NHCH_2CH_2-$;

$X^4$ is H, Me, F, Cl, Br, I, $SO_3H$, $CO_2H$, CN, OMe, $NHCH_2R$, or $NHSO_2R$, wherein R is as defined above, $Y^1$ and $Y^2$ are each independently H, or taken together are $-O-$, $-S-$, $-Se-$, $-CMe_2-$, $-NH-$, $-NMe-$, or $-NPh-$;

A is N, CH, C—CN, C—$CF_3$, C—$CH_2CH_2COOH$, C—CH=CHCOOH, or

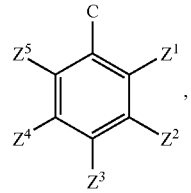

wherein:

$Z^1$ is H, $CO_2H$, or $SO_3H$;

$Z^2$ and $Z^5$ are each independently H, F, or Cl;

$Z^3$ and $Z^4$ are independently H, F, Cl, $CO_2H$, $NO_2$, $NH_2$, NCS, $NHCOCH_2I$, $SCH_2COOH$, $SCH_2CH_2NH_2$, (N-succinimidyl)oxycarbonyl, (N-succinimidyl)oxycarbonylmethylthio, N-maleimidyl, 3,5-dichloro-2,4,6-triazinylamino, CONHQ, or $SO_2NHQ$, wherein Q is H, $C_1$–$C_{20}$ alkyl, $(CH_2)_mCOOH$, $(CH_2)_nNH_2$, or $(CH_2CH_2O)_kCH_2CH_2NH_2$, wherein m is 1 to about 11, n is 2 to about 12, and k is 1 to about 3 or tautomers and physiologically acceptable salts thereof.

In another embodiment, there are provided compounds having the structure:

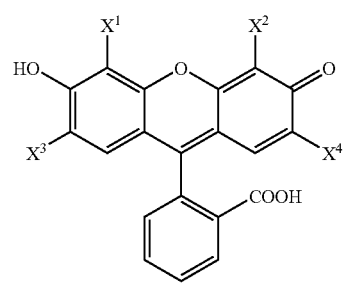

wherein:
X¹ and X² are each independently H, Me, F, Cl, Br, I, SO₃H, CO₂H, CONH₂, CONMe₂, CN, or NO₂; and
X³ and X⁴ are NHCH₂R or NHSO₂R, wherein R is CH₂COOH, CH₂CH₂NG¹G², substituted 2-hydroxyphenyl, or a five or six-membered heterocyclic ring, G¹ and G² are H, Me, Et, CH₂CH₂OH, or together are —(CH₂)₄—, —(CH₂)₅—, —CH₂CH₂OCH₂CH₂—, or —CH₂CH₂NHCH₂CH₂—.

In another embodiment, there are provided kits including at least one invention compound, wherein in the presence of $Zn^{2+}$ ion, the compound is capable of binding to a target sequence in a histidine-rich protein; and a binding partner including a target sequence, the target sequence including a histidine-rich peptide sequence.

In another embodiment, there are provided complexes including an invention compound, a targeting sequence comprising a histidine-rich peptide sequence; and $Zn^{2+}$ ion.

In a further embodiment, there are provided methods of labeling histidine-rich proteins. Such a method can be performed, for example, by providing a fusion protein comprising a native protein and a targeting sequence, and contacting the fusion protein in the presence of an effective amount of $Zn^{2+}$ ion with a compound having the structure:

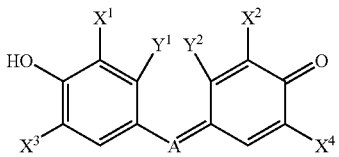

wherein:
X¹ and X² are each independently H, Me, F, Cl, Br, I, SO₃H, CO₂H, CONH₂, CONMe₂, CN, or NO₂;
X³ is NHCH₂R, or NHSO₂R, wherein R is CH₂COOH, CH₂CH₂NG¹G², substituted 2-hydroxyphenyl, or a five or six-membered heterocyclic ring, G¹ and G² are H, Me, Et, CH₂CH₂OH, or together are —(CH₂)₄—, —(CH₂)₅—, —CH₂CH₂OCH₂CH₂—, or —CH₂CH₂NHCH₂CH₂—;
X⁴ is H, Me, F, Cl, Br, I, SO₃H, CO₂H, CN, OMe, NHCH₂R, or NHSO₂R, wherein R is as defined above,
Y¹ and Y² are each independently H, or taken together are —O—, —S—, —Se—, —CMe₂-, —NH—, —NMe-, or —NPh-;
A is N, CH, C—CN, C—CF₃, C—CH₂CH₂COOH, C—CH=CHCOOH, or

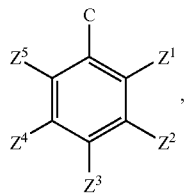

wherein:
Z¹ is H, CO₂H, or SO₃H;
Z² and Z⁵ are each independently H, F, or Cl;
Z³ and Z⁴ are each independently H, F, Cl, CO₂H, NO₂, NH₂, NCS, NHCOCH₂I, SCH₂COOH, SCH₂CH₂NH₂, (N-succinimidyl)oxycarbonyl, (N-succinimidyl)oxycarbonylmethylthio, N-maleimidyl, 3,5-dichloro-2,4,6-triazinylamino, CONHQ, or SO₂NHQ, wherein Q is H, C₁–C₂₀ alkyl, (CH₂)ₘCOOH, (CH₂)ₙNH₂, or (CH₂CH₂O)ₖCH₂CH₂NH₂, wherein m is 1 to about 11, n is 2 to about 12, and k is 1 to about 3 or tautomers and physiologically acceptable salts thereof.

DETAILED DESCRIPTION OF THE INVENTION

Figure 1:
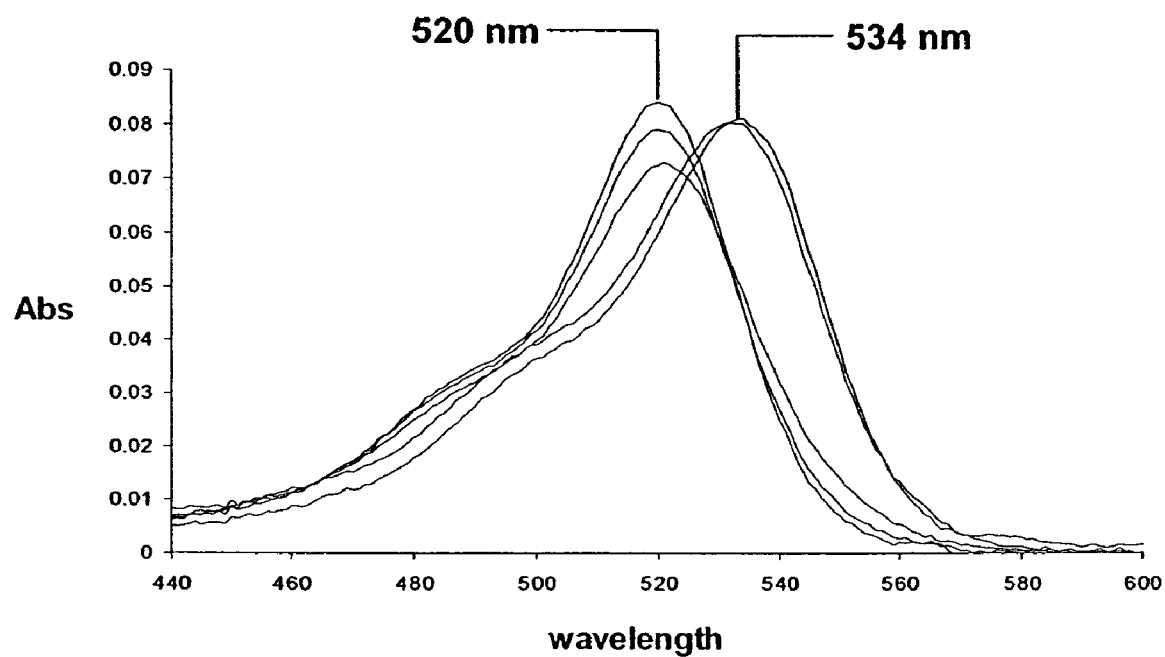
FIG. 1 is graph depicting the absorbance of 2',7'-bis(pyridyl-2-sulfonamido)-4',5'-dimethylfluorescein (I) as a function of free $Zn^{2+}$.

In a first embodiment, the present invention provides Zn-chelating compounds having the structure:

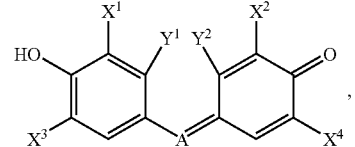

wherein:
X¹ and X² are each independently H, Me, F, Cl, Br, I, SO₃H, CO₂H, CONH₂, CONMe₂, CN, or NO₂;
X³ is NHCH₂R, or NHSO₂R, wherein R is CH₂COOH, CH₂CH₂NG¹G², substituted 2-hydroxyphenyl, or a five or six-membered heterocyclic ring, G¹ and G² are H, Me, Et, CH₂CH₂OH, or together are —(CH₂)₄—, —(CH₂)₅—, —CH₂CH₂OCH₂CH₂—, or —CH₂CH₂NHCH₂CH₂—;
X⁴ is H, Me, F, Cl, Br, I, SO₃H, CO₂H, CN, OMe, NHCH₂R, or NHSO₂R, wherein R is as defined above,
Y¹ and Y² are each independently H, or taken together are —O—, —S—, —Se—, —CMe₂-, —NH—, —NMe-, or —NPh-;
A is N, CH, C—CN, C—CF₃, C—CH₂CH₂COOH, C—CH=CHCOOH, or

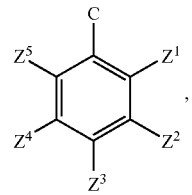

wherein:
Z¹ is H, CO₂H, or SO₃H;
Z² and Z⁵ are each independently H, F, or Cl;

$Z^3$ and $Z^4$ are each independently H, F, Cl, $CO_2H$, $NO_2$, $NH_2$, NCS, $NHCOCH_2I$, $SCH_2COOH$, $SCH_2CH_2NH_2$, (N-succinimidyl)oxycarbonyl, (N-succinimidyl)oxycarbonylmethylthio, N-maleimidyl, 3,5-dichloro-2,4,6-triazinylamino, CONHQ, or $SO_2NHQ$, wherein Q is H, $C_1$–$C_{20}$ alkyl, $(CH_2)_m COOH$, $(CH_2)_n NH_2$, or $(CH_2CH_2O)_k CH_2CH_2NH_2$, wherein m is 1 to about 11, n is 2 to about 12, and k is 1 to about 3 or tautomers and physiologically acceptable salts thereof.

As used herein, the moiety "(N-succinimidyl)oxycarbonyl" has the structure:

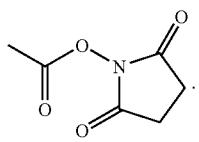

As used herein, the moiety "(N-succinimidyl)oxycarbonylmethylthio" has the structure:

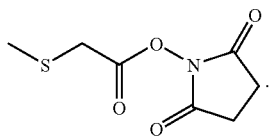

As used herein, the moiety "N-maleimidyl" has the structure:

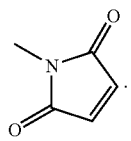

As used herein, the moiety "5-dichloro-2,4,6-triazinylamino" has the structure:

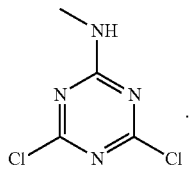

Invention compounds are designed to bind to a specific target sequence by taking advantage of the coordination chemistry of $Zn^{2+}$. Invention compounds include binding moieties that have an affinity for $Zn^{2+}$, but do not completely saturate the coordination sphere of the ion. Thus, the Zn-chelating compound can be bound to the target sequence via the open coordination sites of the $Zn^{2+}$ ion.

Coordination numbers of 4 to 6 are common for the $Zn^{2+}$ ion. Invention compounds typically chelate the $Zn^{2+}$ ion in a tridentate fashion, leaving the $Zn^{2+}$ ion in a coordinatively unsaturated environment. As used herein, the phrase "coordinatively unsaturated environment" means that the $Zn^{2+}$ ion has the ability to complex with at least one more additional ligand. In addition, $Zn^{2+}$ is a cation which readily forms complexes with electron rich heteroatoms such as N, O, S, and the like. Thus, invention compounds typically include heteroatoms to faciliate $Zn^{2+}$ chelation.

In one embodiment, invention compounds include the moiety A having the structure

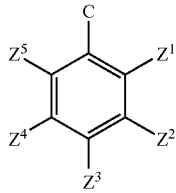

wherein:

$Z^1$ is H, $CO_2H$, or $SO_3H$;

$Z^2$ and $Z^5$ are each independently H, F, or Cl;

$Z^3$ and $Z^4$ are each independently H, F, Cl, $CO_2H$, $NO_2$, $NH_2$, NCS, $NHCOCH_2I$, $SCH_2COOH$, $SCH_2CH_2NH_2$, (N-succinimidyl)oxycarbonyl, (N-succinimidyl)oxycarbonylmethylthio, N-maleimidyl, 3,5-dichloro-2,4,6-triazinylamino, CONHQ, or $SO_2NHQ$, wherein Q is H, $C_1$–$C_{20}$ alkyl, $(CH_2)_m COOH$, $(CH_2)_n NH_2$, or $(CH_2CH_2O)_k CH_2CH_2NH_2$, wherein m is 1 to about 11, n is 2 to about 12, and k is 1 to about 3

In another embodiment, $Z^1$ is $CO_2H$, and $Z^2$, $Z^3$, $Z^4$, and $Z^5$ are each independently H.

In further embodiments, invention compounds have the structure:

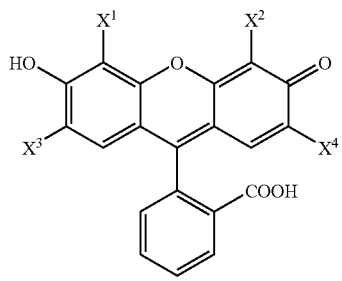

wherein:

$X^1$ and $X^2$ are each independently H, Me, F, Cl, Br, I, $SO_3H$, $CO_2H$, $CONH_2$, $CONMe_2$, CN, or $NO_2$; and $X^3$ and $X^4$ are each independently H, Me, F, Cl, Br, I, $SO_3H$, $CO_2H$, CN, OMe, $NHCH_2R$, or $NHSO_2R$, wherein R is $CH_2COOH$, $CH_2CH_2NG^1G^2$, substituted 2-hydroxyphenyl, or a five or six-membered heterocyclic ring, $G^1$ and $G^2$ are H, Me, Et, $CH_2CH_2OH$, or together are —$(CH_2)_4$—, —$(CH_2)_5$—, —$CH_2CH_2OCH_2CH_2$—, or —$CH_2CH_2NHCH_2CH_2$—.

In a preferred embodiment, $X^3$ and $X^4$ are each independently $NHCH_2R$ or $NHSO_2R$, wherein R is $CH_2COOH$, $CH_2CH_2NG^1G^2$, substituted 2-hydroxyphenyl, or a five or six-membered heterocyclic ring, and wherein $G^1$ and $G^2$ are H, Me, Et, $CH_2CH_2OH$, or $G^1$ and $G^2$ taken together are —$(CH_2)_4$—, —$(CH_2)_5$—, —$CH_2CH_2OCH_2CH_2$—, or —$CH_2CH_2NHCH_2CH_2$—. An exemplary compound according to this embodiment has the structure

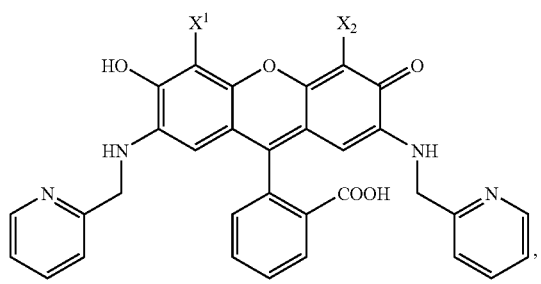

wherein:

$X^1$ and $X^2$ are each independently Me or Cl.

In another preferred embodiment, $X^3$ and $X^4$ are each independently $NHSO_2R$, wherein R is $CH_2COOH$, $CH_2CH_2NG^1G^2$, substituted 2-hydroxyphenyl, or a five or six-membered heterocyclic ring, and wherein $G^1$ and $G^2$ are H, Me, Et, $CH_2CH_2OH$, or $G^1$ and $G^2$ taken together are $-(CH_2)_4-$, $-(CH_2)_5-$, $-CH_2CH_2OCH_2CH_2-$, or $-CH_2CH_2NHCH_2CH_2-$. Exemplary compounds according to this embodiment include

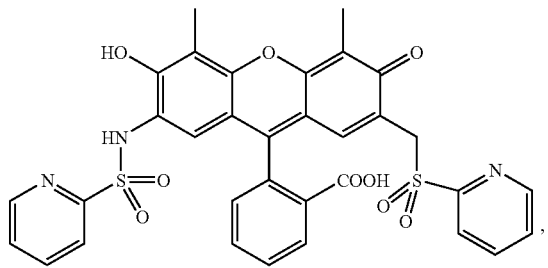

I

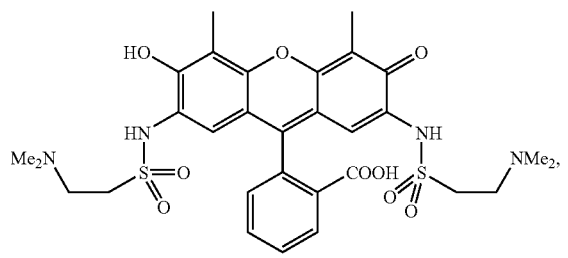

II

-continued

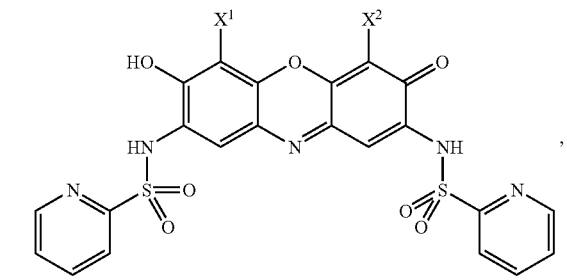

III and

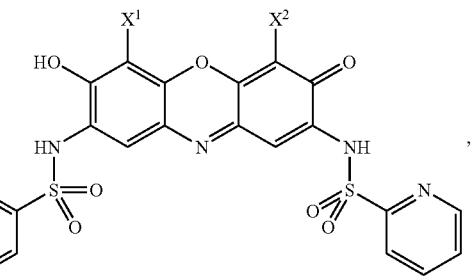

IV

In yet another embodiment, the moiety A in invention compounds is a nitrogen atom. An exemplary compound according to this embodiment has the structure

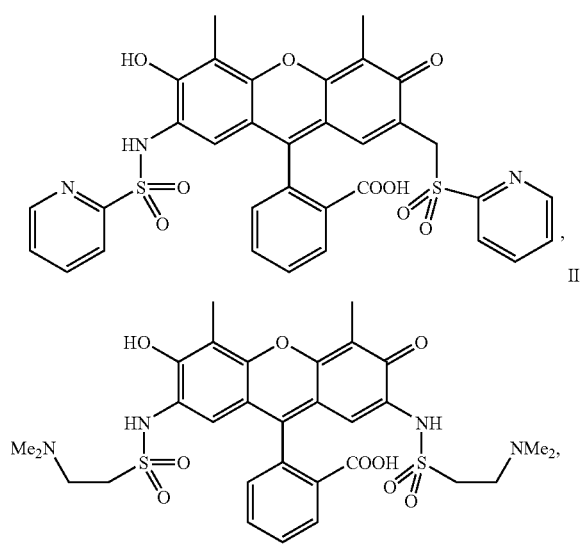

wherein $X^1$ and $X^2$ are each independently H or Me.

In still further embodiments, two invention compounds may be linked via a suitable linking moiety to form homodimers or heterodimers. An exemplary homodimer involving invention compound I is set forth below:

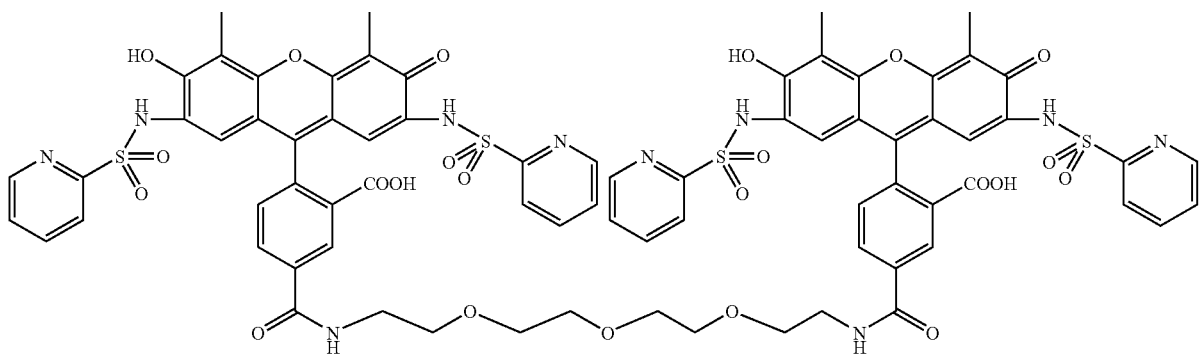

These homodimers are tetrafunctional Zn chelating compounds and can be used to cross-link between two bonding partners, which each include a target sequence.

An exemplary heterodimer is set forth below:

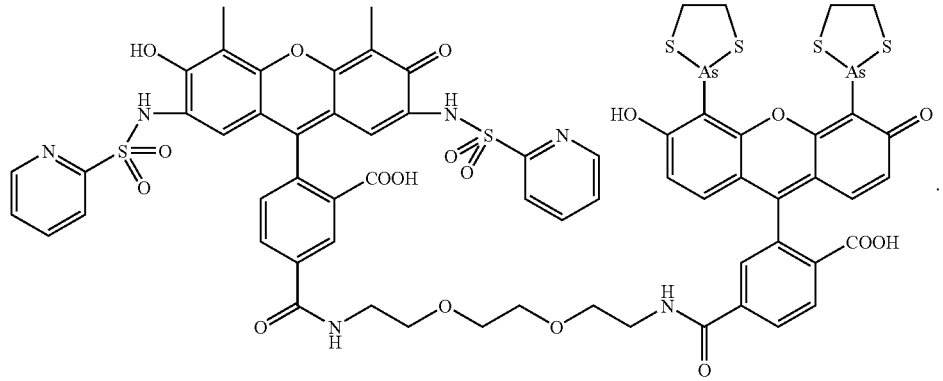

In a preferred embodiment, each bonding partner contains a target sequence and a carrier molecule. The carrier molecule may be a polypeptide. The polypeptides in each of the bonding partners may be the same. Alternatively, the polypeptides in each bonding partner may be different. The target sequences may be the same or they may be different in each bonding partner. For example, cross-linking of polypeptides may be valuable in studying the effects of polypeptide dimerization on signal transduction. Ho S. N., Biggar S. R., Spencer D. M., Schreiber S. L., and Crabtree G. R., Nature 382: 822–826 (1996); Spencer D. M., Wandless T. J., Schreiber S. L., and Crabtree G. R. Science 262: 1019–1024 (1993). The carrier polypeptide may be an enzyme or an antibody.

Invention Zn-chelating compounds include chromophores capable of generating a detectable signal in response to an external stimulus. Such chromophores include, for example, fluorescent groups, phosphorescent groups, luminescent groups, and the like. In some embodiments, chromophores contemplated for use as components of invention compounds are fluorophores such as for example, optionally substituted fluoresceins, resorufins, phenothiazines, phenazines, carbazones, and the like. In one embodiment, the fluorophore is optionally substituted fluorescein or resorufin. In a preferred embodiment, the fluorophore is optionally substituted fluorescein. Examples of detectable signals that can be monitored include fluorescence, fluorescence anisotropy, time-resolved luminescence, phosphorescence amplitude and anisotropy, and the like.

In some embodiments, the Zn chelating compound may be substituted at one or more positions to add a solid phase binding group or a cross-linking group. Indeed, the Zn chelating compound may be coupled to a solid phase.

In some embodiments, the Zn chelating compound is capable of traversing a biological membrane. The small size of the Zn chelating compound can contribute toward the ability of the Zn chelating compound to traverse a biological membrane. Zn chelating compounds of less than 800 Daltons are preferable for membrane traversal.

The polarity of the Zn chelating compound can also influence the ability of the Zn chelating compound to traverse a biological membrane. Generally, a hydrophobic Zn chelating compound is more likely to traverse a biological membrane. The presence of polar groups can reduce the likelihood of a molecule to traverse a biological membrane. A Zn chelating compound that is unable to traverse a biological membrane may be derivatized. The Zn chelating compound may be derivatized by addition of groups that enable or enhance the ability of the Zn chelating compound to traverse a biological membrane. Preferably, such derivatization of the Zn chelating compound does not significantly alter the ability of the Zn chelating compound to subsequently react with the target sequence. The Zn chelating compound may also be derivatized transiently. In such instances, after traversing the membrane, the derivatizing group is eliminated to regenerate the original Zn chelating compound. Examples of derivatization methods that increase membrane traversability include esterification of phenols, ether formation with acyloxyalkyl groups, reduction of chromophores to uncharged leuco compounds, and the like.

Also within the scope of this invention is a Zn chelating compound that may be detectable before and after it specifically reacts with a target sequence to form the Zn chelating compound/target sequence complex. In such instances, it is preferable if the signal of the Zn chelating compound can be differentiated from the signal of the complex. For example, if the detectable signal of the Zn chelating compound is a fluorescent signal, it would be preferable if the fluorescence of the complex is red-shifted or blue-shifted relative to the Zn chelating compound alone.

The Zn chelating compound may also lack a detectable signal, both before and even after specifically reacting with a target sequence. These Zn chelating compounds can be useful in many techniques that do not require a detectable signal, or that use other methods of detection. These Zn chelating compounds may be useful when the goal is to attach a polypeptide to a solid substrate, cross-link two polypeptides or encourage a polypeptide domain to become α-helical.

A particularly useful advantage of the specific reaction between the Zn chelating compound and a target sequence is the reversibility of the reaction. A complex containing the Zn chelating compound and the target sequence may be dissociated by providing an excess of a reagent such as EDTA or any other strong Zn chelator.

Invention compounds can be synthesized in a variety of ways using the methods of synthetic organic chemistry. An exemplary synthesis of compound (I) is set forth in Scheme I.

Scheme I

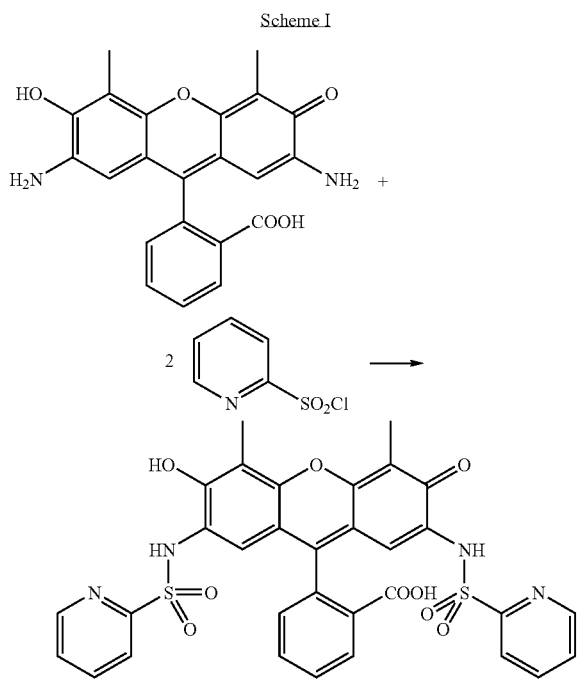

As depicted above, compound (I) can be synthesized by reacting 4',5'-dimethyl-2',7'-diaminofluorescein with 2 equivalents of pyridyl-2-sulfonyl chloride.

In compound (I), each sulfonamido-pyridine group functions as a bidentate $Zn^{2+}$ chelating moiety. The chromophore is the fluorophore fluorescein. Compound (I) can be bound to a target sequence in a recombinant fusion protein via the $Zn^{2+}$ ion as shown in the complex (I) below. In the complex below, the target sequence is a histidine-rich peptide sequence having six histidine residues. It will be understood, however, that any histidine-rich peptide sequence is contemplated for use in the practice of the invention The coordination environment depicted in complex (I) is set forth for exemplary purposes only. It is understood that a wide variety of coordination environments are possible between the invention $Zn^{2+}$ chelating compound and the targeting sequence of the recombinant fusion protein.

The histidine-rich peptide sequence may include other amino acids with the caveat that the other amino acids do not interfere with the binding of the Zn-chelator molecule. The histidine-rich peptide sequence preferably contains about 6 histidine residues. In one embodiment, the histidine-rich peptide sequence is -$His_6$-.

Since the $Zn^{2+}$ ion is less toxic than Ni, invention compounds can be used to label proteins in living cells. In addition, invention Zn chelating compounds are small and unlikely to disturb protein folding and function. Moreover, the Zn chelating compounds can be rapidly washed away with EDTA or other strong $Zn^{2+}$ chelators. Accordingly, invention compounds can be used as a reversible fluorescent labeling system on living cells.

Indeed, invention Zn-chelating compounds, in combination with the target sequence, form a Zn-chelating compound/target sequence complex that is useful in a number of methods. The complex is particularly useful in methods for labeling a carrier molecule. The carrier molecule can be associated with the target sequence to form a bonding partner. In preferred embodiments, the carrier molecule is a polypeptide.

A bonding partner that includes a target sequence is contacted with a Zn chelating compound. Contact of the Zn chelating compound with the bonding partner is performed under conditions appropriate for a specific coordination to occur between the Zn chelating compound and the target sequence to form the Zn chelating compound/target sequence complex.

A Zn chelating compound/target sequence complex that generates a detectable signal may be used if detection of a labeled carrier molecule is desired. A particular advantage of using the Zn chelating compound and the target sequence for labeling is the specificity and the reversibility of the interaction. The Zn chelating compound/target sequence com- Complex I

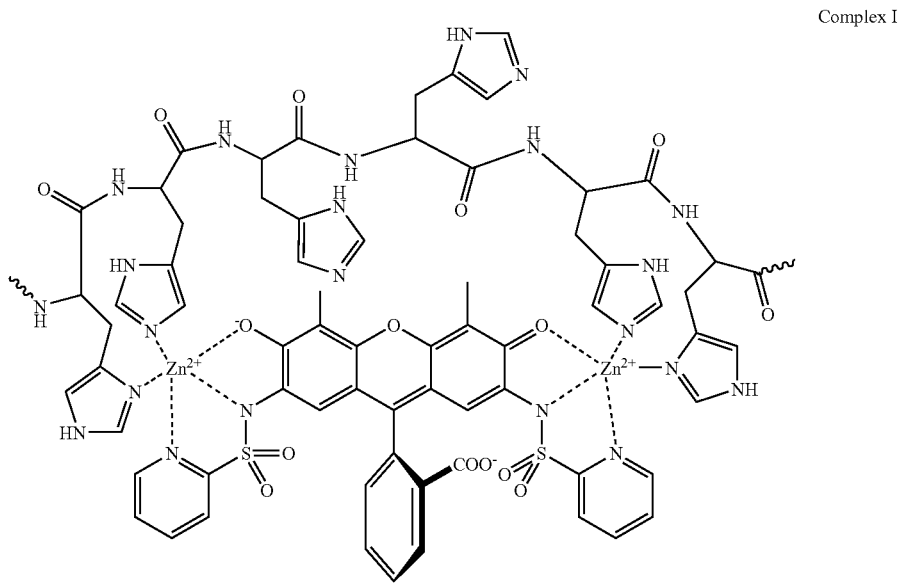

plex may be dissociated, for example, after the detection of the complex by reaction of the strong Zn chelator EDTA.

The Zn chelating compound may be added to a composition that includes the target sequence. The Zn chelating compound may or may not be capable of traversing a membrane. The bonding partner may be, for example, in a test tube, a microtiter well or immobilized on a solid phase. Uses of the Zn chelating compound/target sequence complex include polypeptide purification, immunoassays, and other biological and chemical assays.

Immobilization of either the Zn chelating compound or the bonding partner to a solid phase may be particularly useful. Immobilization may include adsorption, absorption or covalent bonding. A solid phase may be inert or it may be reactive for coupling. Solid phases that may be used include glass, ceramics, and natural or synthetic polymeric materials. Examples of polymeric materials include cellulose-based materials, dextran-based materials, and polystyrene-based materials.

The Zn chelating compound may be contacted with a bonding partner in a living cell. The bonding partner may be introduced into a cell or produced within a cell. A Zn chelating compound capable of traversing a biological membrane is preferable when the Zn chelating compound is introduced outside the cell and the bonding partner is inside the cell. Typically, a membrane traversing Zn chelating compound is preferable for use within a living cell. Examples of uses of the Zn chelating compound/target sequence complex within cells include polypeptide interactions, polypeptide location, polypeptide quantifications, nucleic acid molecule identification and location.

The Zn chelating compound may be used to induce a more favorable conformation of the bonding partner. For example, the bonding partner may have two possible conformations, but one of the conformations may be more functionally important. The bonding partner when it specifically reacts with the Zn chelating compound may adopt the more functionally important conformation. A functionally important conformation may be, for example, a conformation that can bind a drug.

In some embodiments, a bonding partner containing the target sequence and an antibody as the carrier polypeptide may be cross-linked via a tetrafunctional Zn chelating compound to a bonding partner containing the target sequence and an enzyme as the carrier polypeptide. Such a composition may be useful, for example, in enzyme immunoassays.

A wide variety of assays exist that use detectable signals as a means to determine the presence or concentration of a particular molecule. Examples of such assays include immunoassays to detect antibodies or antigens, enzyme assays, chemical assays and nucleic acid assays. An above described Zn chelating compound/target sequence complex can be useful in these assays.

In general, assays may be performed as follows. A sample containing a molecule of interest associated with either the Zn chelating compound or the target sequence may be contacted with the target sequence or the Zn chelating compound, respectively. The resulting solution is then monitored for the presence of a detectable signal or a change in a detectable signal.

The invention will be further understood with reference to the following examples, which are purely exemplary, and should not be taken as limiting the true scope of the present invention as described in the claims.

EXAMPLES

Example 1

Synthesis of Exemplary Zn-Chelating Compounds, 2',7'-Bis(pyridyl-2-sulfonamido)-4',5'-dimethylfluorescein, and 2',7'-Bis(pyridyl-2-methylamino)-4',5'-dimethylfluorescein Phthalic anhydride, 2-methylresorcinol, 2-mercaptopyridine, fluorescein and $ZnCl_2$ were purchased from Aldrich and received without further purification. Solvents were purchased from Fisher (HPLC grade) and dried by storage over 4 Å molecular sieves unless noted otherwise. 2-Pyridinesulfonyl chloride (*J. Org. Chem.* 1999, 64, 5896–5903) and 2-chlororesorcinol (*JACS*, 1941, 63, 544) were prepared according to literature procedures.

4',5'-dimethylfluorescein

In a round bottom flask, phthalic anhydride (16.7 g, 113 mmol) and 2-methylresorcinol (24.9 g, 201 mmol) were combined and melted into a brown liquid at 150° C. Fused $ZnCl_2$ (15 g, 110 mmol) was added over 40 min, and the temperature was slowly increased to 230° C. until all material solidified. The brick red solid was pulverized and boiled in 6M HCl for 30 min. The red solid was collected on a glass frit, washed with water, and dried in air over night (yield: 32.62 g, 91% of the theoretical yield).

2',7'-dinitro-4',5'-dimethylfluorescein

Crude 4',5'-dimethylfluorescein (0.73 g, 2 mmol) was dissolved in 30 g of $H_2SO_4$(conc). To this solution was added 0.5 g $HNO_3$ (sp. gr. ~1.42) in 2 g $H_2SO_4$(conc). The reaction mixture was stirred overnight and the resulting yellow solution poured on to crushed ice. The yellow precipitate was collected on a glass frit, washed thoroughly with ice water and dried in air.

2',7'-diamino-4',5'-dimethylfluorescein

2',7'-dinitro-4',5'-dimethylfluorescein (0.2 g, 0.44 mmol) was dissolved in 30 mL of absolute ethanol (~200 proof) and 0.2 g of palladium catalyst (5% palladium on activated peat carbon) was added. The yellow solution was stirred under $H_2$ until 66.4 mL (~2.656 mmol) of $H_2$ had been taken up, at which point the solution was bright red. The solution was filtered through Celite to remove the catalyst and the filtrate was evaporated to dryness. The remaining brown-black residue was dried in vacuo for 2 h (yield: 0.16 g, 93% of the theoretical yield).

2',7'-Bis(pyridyl-2-sulfonamido)-4',5'-dimethylfluorescein (I)

2',7'-Diamino-4',5'-dimethylfluorescein (15 mg, 0.038 mmol) was dissolved in 1 mL of dry, freshly distilled pyridine and 2-pyridinesulfonyl chloride (40 mg, 0.225 mmol) was added. The reaction mixture was stirred overnight. The brown solution was then added to 20 mL of water and an orange solid precipitated immediately. The precipitate was redissolved in 10 mL 1N—NaOH and precipitated with HCl(conc). The crude product was dried in vacuo and then purified by HPLC and identified by electrospray mass spectrometry in 50% MeOH, 1% HOAc, positive ion mode: found for (M+1) 673.0. Calcd for $C_{32}H_{25}N_4O_9S_2$ 673.11.

2'7'-Bis(pyridyl-2 methylamino)-4'5'-dimethylfluorescein

2',7'-Diamino-4'5'-dimethylfluorescein (0.03 g, 0.08 mmol) was dissolved in 3 mL of absolute EtOH and 2-pyridinecarboxaldehyde (0.12 mL, 1.26 mmol) was added. The reaction mixture was stirred overnight and the next morning an orange precipitate was isolated by filtration. The solid was dissolved in 2 mL of EtOH and $NaBH_4$ (0.01 g, 0.26 mmol) was added. After stirring for about 1 h the resulting purple solution was added to 10 mL of water and the pH was adjusted to ~pH 5 with 1N—HCl. A red-purple solid precipitated, was collected on a glass frit, dried in vacuo and purified by HPLC. The product could be identified by electrospray mass spectrometry in 50% MeOH, 1% HOAc, positive ion mode: (M+1) 573.2; Calcd for $C_{34}H_{29}N_4O_5$ 573.21.

2'7'-Bis(pyridyl-2-methylamino)-4'5'-dichlorofluorescein

4'5'-Dichlorofluorescein, 4'5'-dichloro-2'7'-dinitrofluorescein and 4'5'-dichloro-2'7'-diaminofluorescein were prepared following the procedures described above for the 4'5'-dimethylfluorescein derivatives. 4'5'-Dichloro-2'7'-diaminofluorescein (0.03 g, 0.07 mmol) was dissolved in 2.5 mL of absolute EtOH and 2-pyridylcarboxaldehyde (0.12 mL, 1.26 mmol) was added. The brown reaction mixture was stirred overnight. The next morning $NaBH_4$ (0.01 g, 0.26 mmol) was added and the resulting pink-red solution was stirred for 2 h. To this solution was then added 5 drops of glacial acetic acid and the mixture poured into 10 mL of water. A red solid precipitated immediately, was collected on a glass frit, washed with water and dried in vacuo. The crude product was purified by HPLC and could be identified by electrospray mass spectrometry in 50% MeOH, 1% HOAc, positive ion mode: (M+1) 613.3 Calcd for $C_{32}H_{23}Cl_2N_4O_5$ 613.10.

Formation of Zn-Complex

Figure 2:
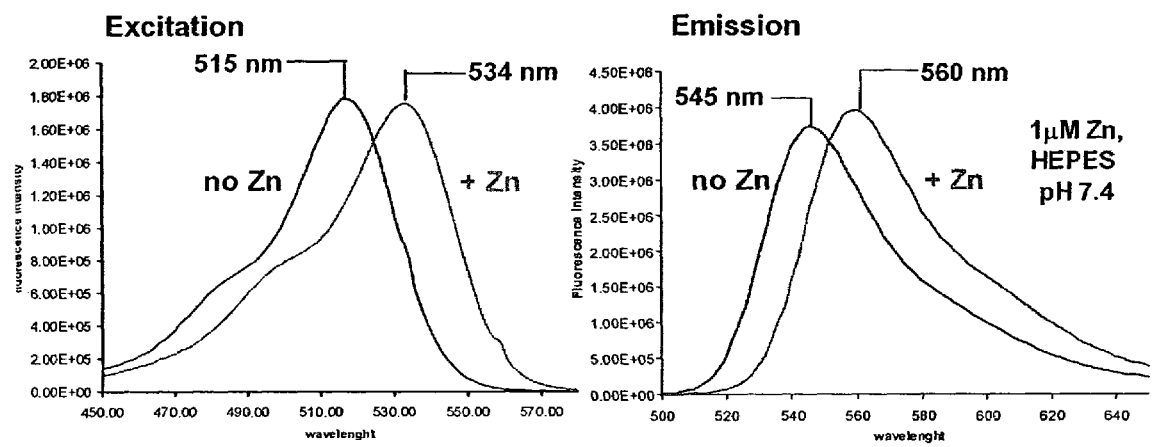
FIG. 2 depicts the excitation and emission spectrum at 0 and 1 μM free $Zn^{2+}$.

Formation of the Zn-complex can be monitored by absorbance or fluorescence emission and excitation shifts. Aliquots of a dye stock solution in DMSO were added to 500 µL of buffers containing 10 nM, 100 nM, 1 µM or 10 µM free zinc (controlled by $Ca^{2+}/Zn^{2+}$ EGTA and 10 mM HEPES; see Walkup, G. K., Burdette, S. C., Lippard, S. J., and Tsien, R. Y., J. Am. Chem. Soc. 2000, 122, 5644–5645) or zinc free (10 mM HEPES, 1 mM EDTA buffer) solutions to yield approximately 1–1.5 µM dye solution ($\epsilon$~65,500 $M^{-1}$ $cm^{-1}$). A progressive shift in the absorbance maxima can be observed with free $Zn^{2+}$ increasing from zero up to 1 µM, with no further shift at 10 µM free $Zn^{2+}$ (FIG. 1). Comparable $Zn^{2+}$-induced shifts to longer wavelengths are observed in the fluorescence excitation and emission spectra, while the fluorescence quantum yield (~0.4) remains virtually unchanged (FIG. 2).

Binding to $His_6$-mRFP Protein In Vitro

Samples of $His_6$-tagged mRFP (see below) and non-tagged mRFP were gifts from Robert E. Campbell, University of California, San Diego (mRFP=monomeric red fluorescent protein, Campbell et al, Proc. Natl. Acad. Sci. USA 2002, 99, 7877–7882).
MRGSHHHHHHGMASMTGGQQMGRDLYDDDDKDP-mRFP His-tag and zinc-dependent binding of compound (I) to the $His_6$-sequence was determined by addition of 1–1.5 µM of compound (I) to 5 µM of $His_6$-mRFP or non-tagged mRFP in $Zn^{2+}$-free and 1 µM free $Zn^{2+}$ buffers, respectively.

Figure 3:
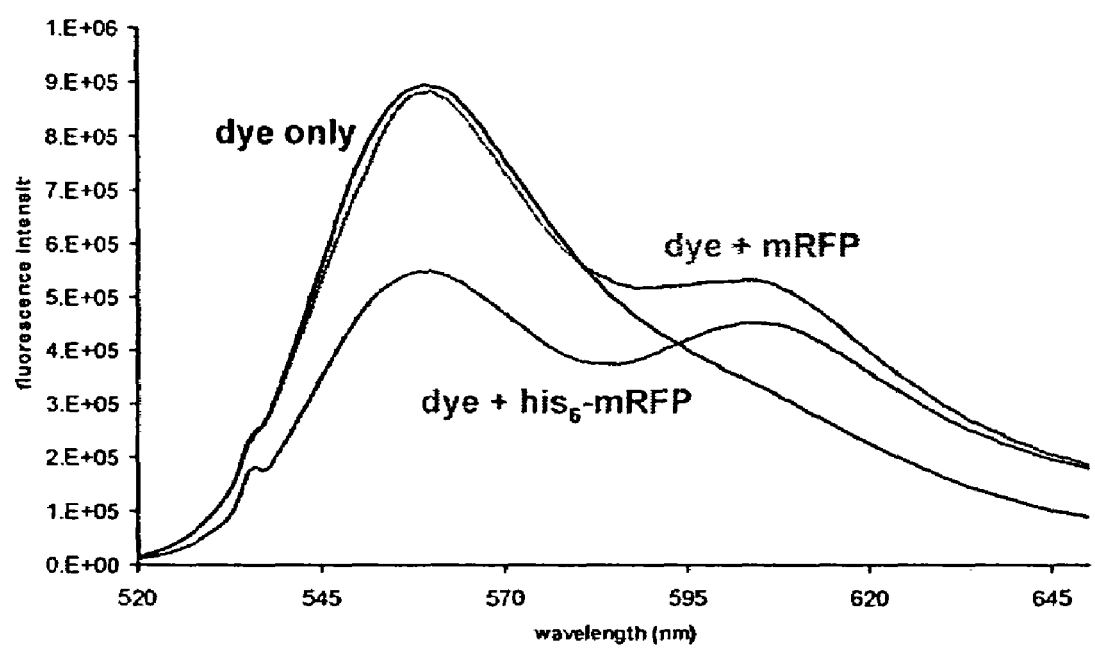
FIG. 3 depicts the emission spectra of dye alone or with untagged or His₆-mRFP, all at 1 μM free $Zn^{2+}$.
Figure 4:
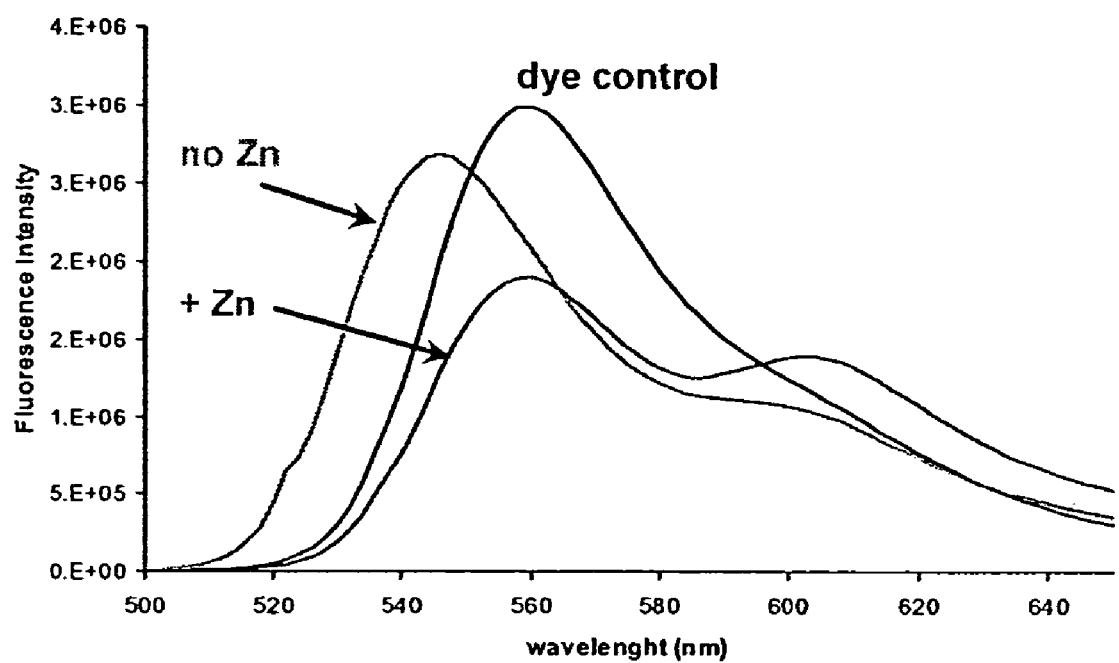
FIG. 4 depicts the emission spectra of dye plus His₆-mRFP at 0 ("no Zn") or 1 μM ("+Zn") free $Zn^{2+}$ compared with dye without any protein at 1 μM free $Zn^{2+}$ ("dye control").

FRET from the donor molecule (Zn-complex of compound (I)) to the acceptor ($His_6$-mRFP) protein is observed as a quenching of the 560 nm emission from the dye, which occurs only with $His_6$-mRFP but not with untagged mRFP. Such FRET demonstrates binding of the donor to the $His_6$ sequence (FIG. 3). FIG. 4 shows that FRET requires the presence of $Zn^{2+}$ and results not only in a loss of 560 nm emission from the dye donor but also a sensitized re-emission at ~605 nm from the mRFP1.

Synthesis of $His_6$-pDisplay Target Sequence

A gene encoding the peptide MRGSHHHHHHG-MASMTGGQQMGRDLYDDDDKDP ($His_6$-) was created by the polymerase chain reaction (PCR), using pRSETB template (Invitrogen). BglII and SacII restriction sites were incorporated at the 5' and 3' ends of the gene, by using the forward primer GGGGAGATCTATGCGGGGTTCTCAT-CAT and reverse primer GAATCCGCGGCGGATCCT-TATCGTC. For expression on the surface of mammalian cells, the gene was inserted into the pDisplay vector (Invitrogen) using the BglII and SacII restriction sites. This vector supplies the necessary sequences for entry into the secretory pathway and anchoring to the outer face of the plasma membrane.

Cell Culture and Imaging

HEK 293 cells were plated onto sterilized glass cover slips on 2 cm dishes or 10 cm plates and grown to 50–100% confluency in DMEM supplemented with 10% FBS at 37° C. in 6% $CO_2$. Cells were transfected with FUGENE-6 transfection reagent (Roche Molecular Biochemicals). After 24 to 48 h incubation at 37° C. in culture medium, the cells were washed once with Hanks' balanced salt solution buffer (HBSS). Then 2 mL of the staining solution (HEPES buffer with 1 µM free $Zn^{2+}$ (pH 7.4), ~1–1.5 µM of compound (I) (DMSO stock)) was added to the cells. After 1 min, the cells were washed twice with HBSS and imaged. Imaging experiments were performed with excitation at 540 nm (25 nm bandwidth), emission at 595 nm (50 nm bandwidth), and dichroic mirror at 560 nm for the Zn-compound (I); and excitation at 420 nm (20 nm bandwidth), emission at 475 nm (40 nm bandwidth) and dichroic mirror at 450 nm for CFP.

Figure 5:
FIG. 5 depicts transient transfection and staining protocol for HEK cells with his₆ display DNA.
Figure 5:
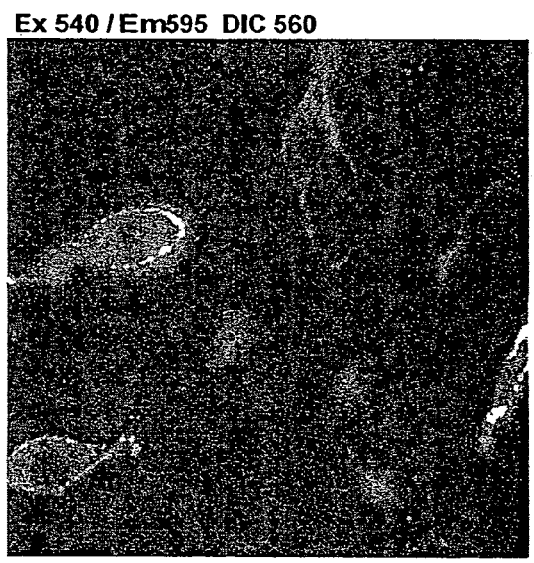
Figure 6:
FIG. 6 depicts CFP fluorescence and Dye fluorescence of HEK 293 cells transiently expressing CFP and a membrane targeted his₆ protein.
Figure 7:
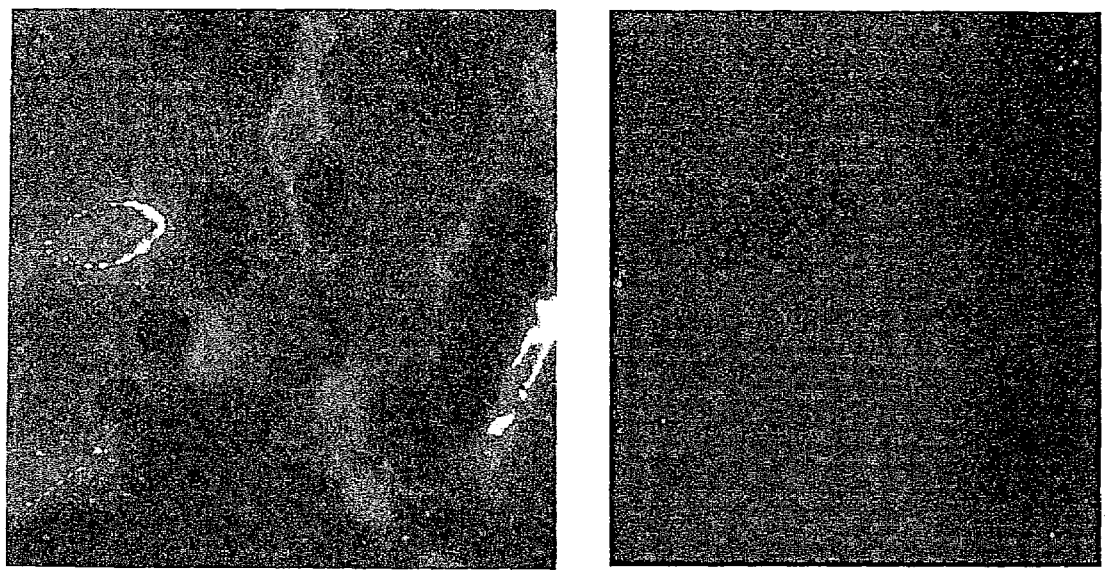
FIG. 7 illustrates the facile reversibility of staining using invention compounds. The Zn-chelating compounds can be washed away with a strong chelator such as EDTA.

A solution of Compound (I) in buffer containing 1 µM $Zn^{2+}$ was added extracellularly to intact HEK293 cells expressing a $His_6$-tagged test-protein, targeted to the surface of the cell membrane. As shown in FIGS. 5 and 6, after subsequent washing (Compound (I) stains cells virtually instantaneously), transfected cells clearly showed membrane specific fluorescent staining; neighboring non-transfected cells showed no staining. A control experiment with cells co-expressing cytosolic CFP, proved that, after application of Compound (I), only transfected cells exhibit membrane specific staining. As shown in FIG. 7, staining is reversible by washing with EDTA solutions, presumably because EDTA chelates all available $Zn^{2+}$. Fluorescent resonance energy transfer from Compound (I) to a $His_6$-tagged fluorescent protein (mRFP-$His_6$) was observed, proving binding to the protein. Fluorescence anisotropy measurements also clearly indicate binding to a poly-histidine peptide.

Example 2

Chemical Structures and Fluorescent Properties of Invention Compounds I, II, and IV

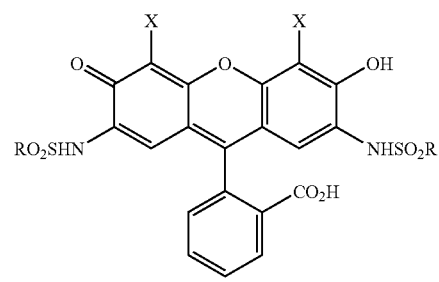

-continued

Compound I, X = Me, R = 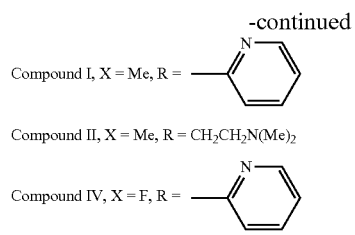

Compound II, X = Me, R = CH$_2$CH$_2$N(Me)$_2$

Compound IV, X = F, R =

Excitation (ex), emission (em) maxima (in nm) and fluorescence quantum yields (φ) are set forth in Table 1.

TABLE 1

|  | −Zn$^{2+}$ | | | +Zn$^{2+}$ | | | +Zn$^{2+}$ + his$_6$-CFP | | |
|---|---|---|---|---|---|---|---|---|---|
|  | ex | em | φ | ex | em | φ | ex | em | φ |
| Compound I | 518 | 545 | 0.40 | 523 | 557 | 0.34 | 536 | 560 | 0.09 |
| Compound IV | 525 | 547 | 0.60 | 533 | 566 | 0.35 | 545 | 570 | 0.08 |
| Compound II | 517 | 544 | 0.47 | 523 | 560 | 0.37 | 531 | 560 | 0.19 |

Excitation (ex), emission (em) maxima (in nm) and fluorescence quantum yields (φ) of 1 µM dye in 100 mM KCl 10 mM MOPS pH 7.2 with 50 µM EDTA (—Zn$^{2+}$), 100 µM ZnCl$_2$ (+Zn$^{2+}$) or 100 µM ZnCl$_2$ and 1 µM his$_6$-CFP (+Zn$^{2+}$+ his$_6$-CFP).

Compound IV (2',7'-bis(2-pyridylsulfonamido)-4',5'-difluorofluorescein) was prepared analogously to the method described for Compound I except 4',5'-dimethylfluorescein was replaced by 4',5'-difluorofluorescein (Synthesis of Fluorinated Fluoresceins. Sun, W.-C.; Gee, K. R.; Klaubert, D. H.; Haugland, R. P.; J. Org. Chem.; 1997; 62(19); 6469–6475) and nitrated and reduced in the usual way.

Compound II (2',7'-bis(2-dimethylaminoethanesulfonamido)-4',5'-difluorofluorescein was prepared analogously to the method described for Compound I except 2-pyridylsulfonyl chloride was replaced in the final step by 2-dimethylaminoethanesulfonyl chloride (Owens, A. H.; Goehring, R. R; Lampe; J. W.; Erhardt, P. W.; Lumma, W. C.; Wiggins, J; Eur. J. Med. Chem. Chim. Ther.; 23; 1988; 295–300). All dyes were purified by reverse-phase HPLC using an acetonitrile-water-trifluoroacetic acid gradient and gave the expected molecular weight with electrospray mass spectroscopy.

Example 3

Binding Affinities of the Zn-Dye Complex (I) to His-Peptides

The binding affinities of the Zn-dye complex (I) to three different peptides were determined by surface plasmon resonance (Biacore). All peptides were synthesized on a Pioneer Peptide Synthesis System (Applied Biosystems) on NovaSyn TGR resin (Novabiochem) using 0.5 M HATU in DMF and 1.0 M N,N-diisopropylethylamine (DIEA) in DMF as the coupling reagents. Syntheses were conducted with a 4-fold excess of Fmoc amino acids, a coupling time of 1 hour. Cleavage and deprotection was accomplished by incubating the peptide in 96% trifluoroacetic acid (TFA), 2% triisopropylsilane (TIS), and 2% anisole for 1 hr. All peptides were N-terminally biotinylated with biotin-XX-N-hydroxysuccinimide ester (Molecular Probes) in 1 M DIEA in DMF. The peptides were HPLC purified on a Dionex instrument equipped with an LC30 Chromatography Oven and PDA-100 Photodiode Array Detector using a C18 column and water/acetonitrile gradient. The purified peptide-biotin-XX adducts were verified by electrospray mass spectroscopy in 50% MeOH, 1% HOAc, positive ion mode. The following peptides were synthesized and analyzed:

| Peptide | K$_D$ |
|---|---|
| Biotin-XX-HHHHHH | 13 nM |
| Biotin-XX-HHHHHHHH | 12 nM |
| Biotin-XX-HHDDDDHH | 170 nM |

Biacore experiments were performed on a Biacore 3000 instrument. Peptides were coupled to streptavidin-coated chips (SA sensor chip, Biacore), which were pre-cleaned three times with 50 mM NaOH in 1 M NaCl. Peptides were coupled to the chip in 10 mM HEPES, 0.05% Tween-20, 500 mM NaCl. Approximately 250 RU of each peptide, corresponding to ~0.2 pmol peptide, were coupled in each flow cell. Flow cell 1 of each sensor chip was used as the reference, and the refractive index change of that flow cell was subtracted from all sensorgrams. Responses to 10, 20, and 100 nM Zn-dye complex, all in a buffer with 1 micromolar free Zn$^{2+}$ maintained by 100 mM KCl, 6 mM SrCl$_2$, 4.03 nM EGTA, 3.028 mM ZnO, 10 mM K-HEPES pH 7.4, 0.05% Tween-20, were fitted globally with the BiaEvaluation software package (Version 3.1) assuming 1:1 interaction with the peptide.

Although the invention has been described with reference to the above example, it will be understood that modifications and variations are encompassed within the spirit and scope of the invention. Accordingly, the invention is limited only by the following claims.

What is claimed is:

1. A compound having the structure:

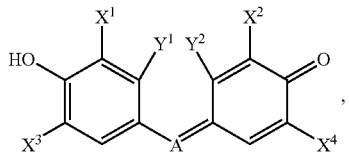

wherein:

each of $X^1$ and $X^2$ is independently F, Cl, Br, or I;

$X^3$ is $NHCH_2R$, or $NHSO^2R$, wherein R is a five or six-membered heterocyclic ring;

$X^4$ is $NHCH_2R$, or $NHSO_2R$, wherein R is as defined above, $Y^1$ and $Y^2$ taken together are —O—, —S—, —Se—, —CMe$^2$-, —NH—, —NMe-, or —NPh-;

A is

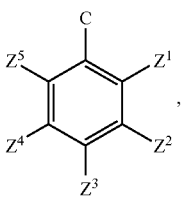

wherein:

$Z^1$ is H, $CO_2H$, or $SO_3H$;

each of $Z^2$ and $Z^5$ is independently H, F, or Cl;

each of $Z^3$ and $Z^4$ is independently H, F, Cl, $CO_2H$, $NO_2$, $NH_2$, NCS, $NHCOCH_2I$, $SCH_2OOOH$, $SCH_2CH_2NH_2$, (N-succinimidyl)oxycarbonyl, (N-succinimidyl)oxycarbonylmethylthio, N-maleimidyl, or 3,5-dichloro-2,4,6-triazinylamino, or tautomers and physiologically acceptable salts thereof.

2. The compound of claim 1, wherein $Z^1$ is $CO_2H$, and $Z^2, Z^2, Z^4$, and $Z^5$ are each independently H.

3. A compound having the structure:

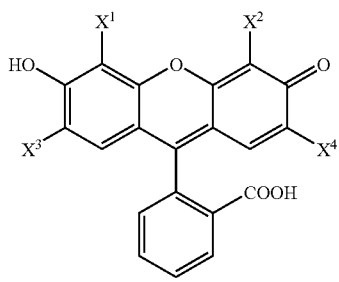

wherein:
each of $X^1$ and $X^2$ is independently F, Cl, Br, or I; and $X^3$ and $X^4$ are $NHCH^2R$ or $NHSO^2R$, wherein R is a five or six-membered heterocyclic ring.

4. The compound of claim 3, wherein each $X^3$ and $X^4$ is independently $NHSO_2R$.

5. The compound of claim 3 having the structure

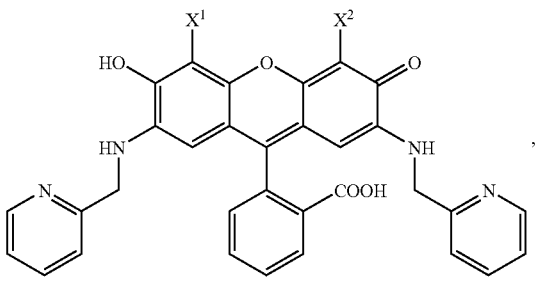

wherein:
each $X^1$ and $X^2$ is independently F, Me or Cl.

6. The compound of claim 4 having the structure:

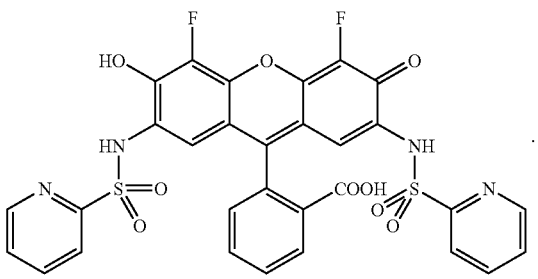

7. An adduct, comprising a product of bonding of the compound of claim 1 to a target sequence in the presence of a chelating substance including $Zn^{2+}$ ion, wherein the adduct is capable of generating a detectable signal.

8. The adduct of claim 7, wherein the detectable signal is a fluorescent signal.

9. The adduct of claim 8, wherein the target sequence is a histidine-rich peptide sequence.

10. The adduct of claim 9, wherein the histidine-rich peptide sequence comprises 6 histidine residues.

11. A kit, comprising:
(a) a compound of claim 1;
(b) a chelating substance including $Zn^{2+}$ ion; and
(c) a target sequence, wherein in the presence of $Zn^{2+}$ ion, the compound of claim 1 is capable of binding to the target sequence in a recombinant fusion protein to generate a detectable signal, the target sequence comprising a histidine-rich peptide sequence.

12. The kit of claim 11, wherein the target sequence comprises 6 histidine residues.

13. The kit of claim 11, wherein the detectable signal is a fluorescent signal.

14. A complex, comprising a product of reaction between:
(a) a compound of claim 1;
(b) a targeting sequence comprising a histidine-rich peptide sequence; and
(c) $Zn^{2+}$ ion.

15. The complex of claim 14, wherein the histidine-rich peptide sequence comprises 6 histidine residues.

16. A method of labeling a histidine-rich protein, comprising contacting a fusion protein including a native protein and a targeting sequence, in the presence of an effective amount of $Zn^{2+}$ ion, with a compound having the structure:

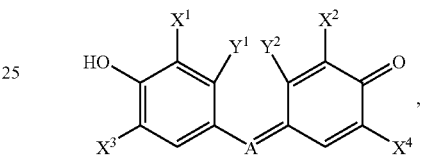

wherein:
each of $X^1$ and $X^2$ is independently F, Cl, Br, or I;
$X^3$ is $NHCH_2R$, or $NHSO_2R$, wherein R is a five or six-membered heterocyclic ring;
$X^4$ is $NHCH_2R$, or $NHSO_2R$, wherein R is as defined above,
$Y^1$ and $Y^2$ taken together are —O—, —S—, —Se—, —CMe$_2$-, —NH—, —NMe-, or —NPh-;
A is

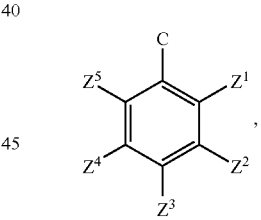

wherein:
$Z^1$ is H, $CO_2H$, or $SO_3H$;
each of $Z^2$ and $Z^5$ is independently H, F, or Cl;
each of $Z^3$ and $Z^4$ is independently H, F, Cl, $CO_2H$, $NO_2$, $NH_2$, NCS, $NHCOCH_2I$, $SCH_2OOOH$, $SCH_2CH_2NH_2$, (N-succinimidyl)oxycarbonyl, (N-succinimidyl)oxycarbonylmethylthio, N-maleimidyl, or 3,5-dichloro-2,4,6-triazinylamino,
or tautomers and physiologically acceptable salts thereof, thereby labeling the histidine-rich protein.

17. The method of claim 16, wherein the histidine-rich protein comprises 6 histidine residues.

18. The method of claim 16, wherein the compound is capable of generating a detectable signal.

19. The method of claim 18, wherein the signal is a fluorescent signal.

* * * * *